US008664359B2

(12) United States Patent
Kazantseva et al.

(10) Patent No.: US 8,664,359 B2
(45) Date of Patent: Mar. 4, 2014

(54) CANCER RELATED ISOFORMS OF COMPONENTS OF TRANSCRIPTION FACTOR COMPLEXES AS BIOMARKERS AND DRUG TARGETS (75) Inventors: Anna Kazantseva, Tallinn (EE); Jekaterina Kazantseva, Tallinn (EE)

(73) Assignee: OncoTx, Inc., Los Angeles, CA (US)

( * ) Notice: Subject to any disclaimer, the term of this patent is extended or adjusted under 35 U.S.C. 154(b) by 469 days.

(21) Appl. No.: 12/598,746

(22) PCT Filed: Jun. 3, 2008

(86) PCT No.: PCT/US2008/065688
§ 371 (c)(1),
(2), (4) Date: Nov. 3, 2009

(87) PCT Pub. No.: WO2008/151200
PCT Pub. Date: Dec. 11, 2008

(65) Prior Publication Data
US 2010/0087376 A1 Apr. 8, 2010

Related U.S. Application Data (60) Provisional application No. 60/941,678, filed on Jun. 3, 2007, provisional application No. 60/941,747, filed on Jun. 4, 2007.

(51) Int. Cl.
C07K 14/00 (2006.01)
G01N 33/53 (2006.01)
G01N 33/574 (2006.01)
C07K 14/435 (2006.01)

(52) U.S. Cl.
CPC .............. C07K 14/00 (2013.01); C07K 14/435 (2013.01); C07K 2319/00 (2013.01); G01N 33/53 (2013.01); G01N 33/574 (2013.01)
USPC ........... 530/350; 435/7.1; 435/7.21; 435/7.23

(58) Field of Classification Search
None
See application file for complete search history.

(56) References Cited

U.S. PATENT DOCUMENTS

| 6,306,993 | B1 * | 10/2001 | Rothbard et al. ............. 526/304 |
| 7,973,135 | B2 * | 7/2011 | Liik et al. .................... 530/387.1 |
| 2003/0105000 | A1 * | 6/2003 | Pero et al. ........................ 514/12 |
| 2004/0219575 | A1 | 11/2004 | Neuman |
| 2007/0048301 | A1 * | 3/2007 | Bodary-Winter et al. . 424/143.1 |
| 2007/0083334 | A1 * | 4/2007 | Mintz et al. ...................... 702/19 |
| 2007/0185017 | A1 * | 8/2007 | Aggarwal et al. ............... 514/12 |
| 2008/0027002 | A1 | 1/2008 | Kazantseva |

FOREIGN PATENT DOCUMENTS

| WO | WO 0153312 A1 * | 7/2001 | |
| WO | WO 01/55450 A2 * | 8/2001 | ............... C12Q 1/68 |
| WO | WO 02/081638 A2 * | 10/2002 | |
| WO | WO 2004039956 A2 * | 5/2004 | |
| WO | WO/2006/005042 A2 | 1/2006 | |
| WO | WO/2008/021290 | 2/2008 | |

OTHER PUBLICATIONS

Gura (Science, 1997, 278:1041-1042).*
Kaiser (Science, 2006, 313: 1370).*
Genosphere Biotechnologies (www.genosphere-biotech.com/Long-Active-Peptides.html "Synthetic peptides with high biochemical activity", Sep. 24, 2012).*
Singh et al. (Glycobiology, 2001, vol. 11, pp. 587-592).*
Rudikoff et al. (PNAS USA, 1982, 79: 1979-1983).*
Coleman et al. (Research in Immunology, 1994; 145(1): 33-36).*
Burgess et al. (J of Cell Biol. 111:2129-2138, 1990.*
Flajollet, S. et al., "Distinct roles of the steroid receptor coactivator and of MED1 . . . differentiation", J of Biological Chem, Jul. 2006, 281 (29):20338-20348.
GenBank Accession No. AAP36584, "*Homo sapiens* general transcription factor . . . 2", May 12, 2003. see http://www. ncbi.nlm.nih. gov/entrez/viewer.fcgi?db=protein&id=30584663.
Giangrande, P. et al., "The opposing activities of the two isoforms of the human progesterone receptor . . . binding", Molec and Cell Biology, May 2000 84(9):3102-3115.
Lee, D. K. et al, "Molecular communication between androgen receptor . . . machinery", J. of Steroid Biochemistry & Molec Biology, Jan. 2003, 84(1):41-49.
O'Malley, B., "Coregulators: from whence came these master genes", Molec. Endocrinology, Published online Feb. 2007, 21(5):1009-1013.
Salma, N. et al., "Temporal recruitment of transcription factors and SWI/SNF chromatin-remodeling . . . receptor", Molec. & Cellular Biolog. Jun. 2004, 24(11):4651-4663.
Wu, J. et al., "Repression of p65 transcriptional activation by the glucocorticoid receptor . . . interactions", 2004, Molecular Endocrinology 18(1):53-62.
European Patent Office Extended Search Report dated Sep. 13, 2011 from corresponding EP Patent Application No. 08770065.4.
Drane, P. et al., "Identification of RB18A, a 205kDa new p53 regulatory protein which shares antigenic . . . p53", Oncogene, 1997;15(25):3013-3024.
Guipaud, O. et al., "An in vitro enzymatic assay coupled to proteomics analysis reveals a new DNA . . . proteins", Proteomics, 2006;6(22):5962-5972.
Risheg, H. et al., "A recurrent mutation in Med12 leading to R961W causes Opitz-Kaveggia syndrome", Nature Genetics, 2007;39(4):451-453.
Vijayvargia, R. et al., "A coregulatory role for the mediator complex in prostate cancer cell proliferation . . . expression", Cancer Research, 2007;67(9):4034-4041.
Wada, O. et al., "BRCA1 function mediates a TRAP/DRIP complex through direct interaction with TRAP220", Oncogene, 2004;23(35):6000-6005.
European Patent Office Action dated May 24, 2012 from corresponding EP Patent Application No. 08770065.4.

* cited by examiner

*Primary Examiner* — Peter J Reddig
(74) *Attorney, Agent, or Firm* — Karen S. Canady; canady + lortz LLP (57) ABSTRACT

The invention is related to isoforms of components of transcription factor complexes that are specifically expressed in cancer cells. These isoforms can be used as biomarkers for detection, diagnosis, prognosis and monitoring of treatments of cancer, and as drug targets of pharmaceutical compositions for the treatment of various cancers expressing the targeted isoforms. Methods, molecules, materials and kits for these uses are disclosed.

16 Claims, 2 Drawing Sheets

CANCER RELATED ISOFORMS OF COMPONENTS OF TRANSCRIPTION FACTOR COMPLEXES AS BIOMARKERS AND DRUG TARGETS

This application claims the benefit of U.S. provisional patent applications, Ser. No. 60/941,678, filed Jun. 3, 2007, and No. 60/941,747, filed Jun. 4, 2007, the entire contents of each of which are incorporated herein by reference.

The instant application contains a lengthy Sequence Listing which has been submitted via text file (.txt) in lieu of a printed paper (or .pdf) copy, and is hereby incorporated by reference in its entirety. The instant application also contains a lengthy Table (Table 1) describing the sequences disclosed herein that has been submitted via text file (.txt) in lieu of a printed paper (or .pdf) copy, and is hereby incorporated by reference in its entirety. The Sequence Listing text file was created as an ASCII text file named "ONC2WOU2.TXT" on May 15, 2008, and is 1,149 KB. Table 1 was created as an ASCII text file named "Table1ascii.txt" on Jun. 3, 2008, and is 146 KB.

Regulation of gene expression at the transcriptional level is a key biological process in determining cell-type and signal-specific gene expression patterns. The above objectives are mainly focused on proteins forming the regulatory networks that control fundamental biological processes in normal and cancer cell contexts Successful execution of cell-specific gene regulation, which combines interdisciplinary efforts, promises new breakthroughs in the field of transcription regulation and cancer, since they address novel aspects in the process, including:

the specific functions of individual basal. RNA polymerase II transcription complexes and how they participate in regulation of gene expression in normal and cancer cells;

how gene specific transcription is achieved during cell differentiation in normal and cancer cells; and how the normal and cancer cell transcription process is spatially organized in the nucleus.

We postulate that a virtually infinite number of transcriptional complexes can recruit the basal transcription machinery in a gene-specific manner to regulate precisely the expression of genes during differentiation, growth and development

LENGTHY TABLES

The patent contains a lengthy table section. A copy of the table is available in electronic form from the USPTO web site (http://seqdata.uspto.gov/?pageRequest=docDetail&DocID=US08664359B2). An electronic copy of the table will also be available from the USPTO upon request and payment of the fee set forth in 37 CFR 1.19(b)(3).

TECHNICAL FIELD OF THE INVENTION

The present invention relates to detection and therapy of cancer. The invention is more specifically related to isoforms of components of transcription factor complexes that are specifically expressed in cancer cells. These isoforms can be used as biomarkers for detection, diagnosis, prognosis and monitoring of treatments of cancer, and as drug targets of pharmaceutical compositions for the treatment of various cancers expressing the targeted isoforms.

BACKGROUND OF THE INVENTION

Cancer remains a significant health problem throughout the world. Current therapies, which are generally based on a combination of chemotherapy or surgery and radiation, continue to prove inadequate in many patients.

The molecular and cell biology of cancer is enormously complex. To date, thousands of genes representing virtually every sub-group of genes have been implicated in the pathophysiology of cancer, including mechanisms regulating uncontrolled growth of tumor cells and metastasis. Currently, it is well established that many cancers, if not all, develop from proliferating stem or progenitor cells with either mutated genes or rearranged chromosomes. As a result of these genetic alterations, tumor cells possess an altered gene and protein expression compared with normal cells (Perou et al., 2000, Hedenfalk et al., 2001, West et al., 2001, Zajchowski et al., 2001). Furthermore, differences in gene expression exist between different types of the same cancer or between histologically similar tumors. For example, data on whole-genome analyses have demonstrated that regulatory networks that determine the expression of specific genes are also different in malignant and non-malignant cells.

in response to external signals (drugs, chemicals, stress etc). The materials and methods disclosed herein serve to decipher how these transcription complexes are deregulated in cancer cells.

Precise temporal and spatial regulation of the transcription of protein-encoding genes by RNA polymerase II (Pol II) is vital to the execution of cellular programs, such as growth, responses to complex developmental and homeostatic signals etc. The molecular circuitry that enables coordinated gene expression is based on DNA-binding transcription factors (TFs) and several transcription co-regulator complexes (TCCs) that modulate chromatin structure and bridge TFs to PolII including, SWI/SNF, MED, GTF and TAF-containing complexes. Numerous data show that different cell types including cancer cells express specific patterns of components of TFs and TCCs. Cell type specific expression of components of TCCs (and their isoforms) is the basis of assembly of transcription complexes with different functions. Different transcription complexes target different sets of DNA binding factors leading to inactivation of different target gene sets and ultimately to realization of different cellular programs.

One of the well-known characteristics of cancer cells is the expression of mRNA splice variants encoding specific isoforms of proteins that are not present in normal cells. A large number of studies report identification of cancer specific or enriched mRNA alternative splice variants. For example, a genome-wide computational screening of 11,014 genes using 3,471,822 human expressed sequence tag (EST) sequences identified 26,258 alternatively spliced transcripts/mRNAs of which 845 were significantly associated with cancer (Wang et al., 2003). Several of the gene-specific splice variants have been shown to have a prognostic value. High level of expression of low molecular weight isoforms of cyclin E has a very strong correlation with survival of both node-negative and node-positive breast cancer patients (Porter and Keyomarsi, 2000, Keyomarsi et al., 2002). Patients with a high expression of the alternative splice variant of helix-loop-helix transcription factor ARNT have a worse relapse-free and overall survival than patients with a low expression (Qin et al., 2001).

Computational analysis of human EST databases identified a large number of mRNA splice variants of regulatory factors (TCCs) that are expressed in a variety of cancer cells. The present invention is based on in silico analysis using a variety of gene expression and EST databases, which has revealed a large number of alternative splice variants of (TCCs) that have cell type and disease specific expression. Splice variants encoding protein isoforms are expressed in cancer cells as relatively abundant isoforms. These isoforms modify transcriptional machinery that results in altered gene expression and may contribute to the development of cancer.

The central role of the transcriptional complexes in the cellular regulatory mechanisms makes them attractive drug targets. Interference at the function or formation of cancer-specific transcription machinery could enable researchers and clinicians to control or correct expression of a large number of genes. TCCs contain at least 100 subunits, whereas their composition in different cell types and on different promoters varies and contains different members of TCC complexes. This cell specific variability of TCC complexes assures specificity of potential treatments that target TCCs. We have isolated a large number of isoforms of components of TCCs with a potentially altered activity from a variety of cancer cells. TAF-containing complexes have been shown to control several aspects of cancer cell proliferation and metastasis (Guipaud et al., 2006). In addition, several isoforms of TAF4 function as dominant negative forms to regulate nuclear hormone receptor targets (Brunkhorst et al., 2004).

SUMMARY OF THE INVENTION

The invention provides an isoform of a transcriptional co-regulator selected from the isoforms shown in SEQ ID NO: 4-207. In one embodiment, the isoform is an isoform of GTF (SEQ ID NO: 6-56). In another embodiment, the isoform is an isoform of TAF (SEQ ID NO: 57-86). In another embodiment, the isoform is an isoform of SWI/SNF (SEQ ID NO: 165-201). In a further embodiment, the isoform is an isoform of MED (SEQ ID NO: 4, 5, 87-164). In yet another embodiment, the isoform is an isoform of a co-activator or co-repressor (SEQ ID NO: 202-207). Also provided is a peptide of at least 6 amino acids in length that specifically binds to an isoform of the invention. The peptide can comprise a fusion protein comprising an isoform of or a peptide of the invention that is fused with a heterologous peptide. In some embodiments, the heterologous peptide is a CPP or NLS, such as one of SEQ ID NO: 1-3, In some optional embodiments, the peptide is fused to a toxic agent.

The invention further provides an antibody that specifically binds an isoform of the invention. In one embodiment, the antibody is labeled with a detectable marker. In another embodiment, the antibody is conjugated to a toxic agent. The isoforms, peptides and antibodies of the invention can be useful in therapeutic and/or diagnostic compositions. Accordingly, the invention also provides a composition comprising one of these molecules and a pharmaceutically acceptable carrier. In addition to a method of treating cancer, the invention also provides a method of killing cancer cells. The method comprising contacting the cancer cells with a peptide of the invention, optionally one conjugated to a toxic agent. Toxic agents are not required, however, as molecules such as peptides, that bind to the isoform is sufficient to interfere with normal functioning of cancer cells by disrupting transcription complexes and therefore altering expression of genes necessary to cancer cell survival.

The invention additionally provides a method for detecting cancer in a tissue specimen. The method comprises detecting the presence of an isoform of claim 1 in the tissue specimen. The presence of the isoform is indicative of cancer. In one embodiment, the detecting comprises contacting a tissue specimen with a detectable molecule that specifically binds an isoform of the invention and detecting binding of the detectable molecule. For example, the detecting may comprise detecting cancer-specific mRNAs or protein isoforms of TCCs. Presence or binding of the detectable molecule is indicative of cancer.

In another embodiment, the invention provides a method for monitoring cancer in a subject. The method comprises assaying a tissue specimen obtained from the subject to measure the amount of an isoform of the invention present in the specimen and comparing the amount of isoform present in the specimen to the amount determined under a previous condition, wherein a change in the amount of the isoform is indicative of a change in the progression of the cancer. For example, an increase in the level indicates the cancer is progressing, while a decrease indicates the cancer is regressing. The previous condition may have been prior to or at an earlier stage in the course of treatment of a cancerous condition, and a decrease in the amount of isoform present can be indicative of treatment efficacy. In one embodiment, the method comprises contacting a tissue specimen obtained from the subject with a detectable molecule that specifically binds an isoform of the invention. The method further comprises determining a level of binding of the detectable molecule with the isoform. Alternatively, the method can comprise detecting the level of isoform present in the specimen. The level of binding of the detectable molecule with the isoform, or the level of isoform present, is then compared to the level of binding determined, or the level of isoform present, under a previous condition. A change in the levels of expression of the TCC isoforms, or of binding of the detectable molecule is indicative of a change in the progression of the cancer.

Representative cancers to be detected, monitored or treated by the methods of the invention include, but are not limited to, melanoma, colorectal cancer, lung cancer, hepatoma, pancreatic cancer, prostate cancer, brain tumors (astrocytoma, glioblastoma, neuroblastoma), sarcoma, chondrosarcoma, breast cancer, ovarian cancer, or teratocarcinoma. In a typical embodiment, the molecule that specifically binds the isoform is a peptide. The peptide is optionally labeled with a detectable marker, e.g., for in vivo imaging.

BRIEF DESCRIPTION OF THE FIGURES

FIG. 1. Analysis of BAF complexes from HeLa and human melanoma SK-Mel 28 and WM266-4 cells. Aliquots of HeLa, SKMel28 and WM 266-4 cell nuclear extracts were chromatographed on ion-exchange PE11 column containing. After washing the column extensively with buffer containing 0.1M KCl, bound proteins were eluted with buffer containing 0.2 (lanes 2, 8 and 14), 0.3M KCl (lanes 3, 9 and 15), 0.5M KCl (lanes 4, 10 and 16), 0.75MKCl (lanes 5, and 11) and 1.0M KCl (lanes 6, and 12). Initial "flow through" is depicted on lanes 1, 7 and 13.

DETAILED DESCRIPTION OF THE INVENTION

The present invention is based on the discovery of cancer-specific isoforms of components of transcription factor complexes, or transcription co-regulatory complexes (TCCs), that are specific to human cancers. These isoforms provide novel targets for treatment and detection of cancer.

Isoforms of Components of TCCs as Novel Promising Drug Targets

Transcriptional regulators determine regulatory networks that control gene-specific transcription. The misregulation of these networks is correlated with a growing number of human diseases that are characterized by altered gene expression patterns. Discovery of cancer specific alterations in composition and function of TCCs suggests that targeting these modified components of TCCs with specific chemical compounds will result in modification of patterns of gene expression that will suppress proliferation and induce apoptosis of specific cancer cells. Since expression of isoforms of transcriptional co-regulators is cancer specific then treatments that target these molecules is likely also cancer specific without significant side effects. For a long time TCCs have been considered to be difficult targets for effective drug development. Recently numerous reports show that small molecules can be developed that interact with specific TFs and TCCs to control activity of specific TCCs.

Cancer and Transcriptional Control

Cancer is a disease of enormous complexity. To date, thousands of genes representing virtually every sub-group of genes have been implicated in cancer. Currently, cancer is thought to develop from proliferating stem or progenitor cells with either mutated genes or rearranged chromosomes. As a result of these genetic alterations, tumor cells also possess an altered gene and protein expression compared with non-malignant cells. Whole-genome analysis of gene expression clearly shows specific differences between normal and cancerous cells as well as between cancer types. This suggests that regulatory networks determining the expression of specific genes are different in malignant and non-malignant cells.

Cancer patients have a highly variable clinical course and outcome. Intrinsic genetic heterogeneity of the primary tumor has been suggested to play a role in this variability and may explain it in part (Chang, et al., 2003). Pathological and clinical factors are insufficient to capture the complex cascade of events that drive the clinical behavior of tumors. Extensive analyses of gene expression patterns of a variety of tumors have resulted in an understanding that histologically similar tumors have different gene expression patterns. Oligonucleotide and cDNA microarray techniques have identified molecular subgroups of specific types of cancer (Perou et al., 2000, Hedenfalk et al., 2001 West et al., 2001, Zajchowski et al., 2001). Molecular profiling of tumors has also been used to predict survival of patients and to select patients for adjuvant therapy (van't Veer et al., 2002, van de Vijever et al., 2002).

Cancer Specific Isoforms of TCCs—Novel Drug Targets with High Specificity

Well-known characteristics of cancer cells are mutations in a variety of regulatory molecules including transcription factors, misexpression of transcription factors, expression of mRNA splice variants encoding specific isoforms of proteins and presence of posttranslational modifications that are not present in normal cells. Mutations and expression of fusion proteins are described in almost every single type of cancer (Leroy H, Roumier C, Huyghe P, Biggio V. Fenaux P, Preudhomme C., CEBPA point mutations in hematological malignancies. Leukemia. 2005 March; 19(3):329-34; Xia and Barr, Chromosome translocations in sarcomas and the emergence of oncogenic transcription factors. Eur J Cancer. 2005 November; 41(16):2513-27). A large number of papers report identification of cancer specific or enriched mRNA alternative splice variants. For example, a genome-wide computational screening of 11014 genes using 3,471,822 human expressed sequence tag (EST) sequences identified 26,258 alternatively spliced transcripts/mRNAs of which 845 were significantly associated with cancer (Wang et al., 2003). Several of the gene-specific splice variants have been shown to have a prognostic value. Patients with a high expression of the alternative splice variant of helix-loop-helix transcription factor ARNT have a worse relapse-free and overall survival than patients with a low expression (Qin et al., 2001). As a rule the expression of cancer-specific or enriched alternatively spliced mRNAs is not related to the mutations in splice donor or acceptor sites but due to the changes in the expression of splicing factors.

We have identified 204 cancer specific or enriched isoforms of GTF (51), TAF (30), SWI/SNF (37), and MED (80) complexes and co-activators and co-repressors (6). Also we have demonstrated that some of the isoforms become integral components of TCCs. These changed TCCs may contribute to the development of cancer. Incorporation of isoforms into functional TCCs confirms that these isoforms are suitable drug targets and drugs that modify function of these isoforms or TCC containing these isoforms can be used to treat cancer.

DEFINITIONS

All scientific and technical terms used in this application have meanings commonly used in the art unless otherwise specified. As used in this application, the following words or phrases have the meanings specified.

As used herein, "peptide" or "polypeptide" includes fragments of proteins, and peptides, whether isolated from natural sources, produced by recombinant techniques or chemically synthesized. Polypeptides (and peptides) of the invention typically comprise at least about 6 amino acids. In some embodiments, the polypeptides are at least about 12 amino acids in length.

As used herein, "CSTC-targeting molecule" (wherein CSTC refers to cancer-specific transcription complex) includes CSTC-targeting peptides, polynucleotides encoding CSTC-targeting peptides, polynucleotides complementary to those encoding CSTC-targeting peptides, peptides that specifically recognize and bind CSTCs, and other small molecules exhibiting the same targeting activity.

A "small molecule" means a molecule having a molecular weight of less than 2000 Daltons, in some embodiments less than 1000 Daltons, and in still other embodiments less than 500 Daltons or less. Such molecules include, for example, heterocyclic compounds, carboxylic compounds, sterols, amino acids, lipids, and nucleic adds.

As used herein, "CSTC-targeting" refers to the specific binding of a CSTC-targeting molecule to a cancer-specific transcription complex, wherein the specificity is such that the CSTC-targeting molecule essentially does not bind normal or native transcription complex.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "tumor protein" is a protein that is expressed by tumor cells. A tumor protein is tumor specific if it is not expressed in non-tumor cells.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "a" or "an" means at least one, unless clearly indicated otherwise.

CSTC-Targeting Peptides

CSTC-targeting peptides and polypeptides as described herein may be of any length. Additional sequences derived from the native protein and/or heterologous sequences may be present, and such sequences retain the ability to modulate transcription complex. In a typical embodiment, the peptide further comprises additional sequence selected to facilitate delivery into cells and into nuclei. For example, a cell penetrating peptide (CPP) can be added, such as the following amino acid sequence: RRRRRRR (SEQ ID NO: 1). Those skilled in the art are aware of other CPPs that can be suitable for use with the invention, such as those described in Ulo Langel, ed., *Cell-Penetrating Peptides: Processes and Applications*, Culinary & Hospitality Industry Publications Services (CHIPS), Weimar, Tex., 2002. An example of a peptide that facilitates nuclear delivery is a nuclear localizing signal (NLS). Typically, this signal consists of a few short sequences of positively charged lysines or arginines, such as PPKKRKV (SEQ ID NO: 2). In one embodiment, the NLS has the amino acid sequence PKKRKV (SEQ ID NO: 3).

In some embodiments, the peptide comprises D-amino acids and/or has been structurally modified to enhance its utility for a given purpose. In some embodiments, the peptide comprises chemically modified amino acids. Aptamers are also encompassed within the invention.

Those skilled in the art will appreciate that certain variants thereof will be useful in the treatment and detection of cancer. A peptide "variant," as used herein, is a peptide that differs from a native CSTC-targeting peptide in one or more substitutions, deletions, additions and/or insertions, such that the transcription complex targeting activity of the peptide is not substantially diminished. In other words, the ability of a variant to bind the transcription complex may be enhanced or unchanged, relative to the native peptide, or may be diminished by less than 50%, and preferably less than 20%, relative to the native peptide. Such variants may generally be identified by modifying one of the above peptide sequences and evaluating the binding of the modified peptide with the targeted transcription complex as described herein. Peptide variants preferably exhibit at least about 85%, more preferably at least about 90% and most preferably at least about 95% identity (determined as described above) to the identified peptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant peptides differ from a native sequence by substitution, deletion or addition of five amino acids or fewer.

Recombinant peptides encoded by DNA sequences as described herein may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant peptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or peptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant peptide.

Portions and other variants having fewer than about 100 amino acids, and generally fewer than about 50 amino acids, may also be generated by synthetic means, using techniques well known to those of ordinary skill in the art. In some embodiments, polypeptides of 10-50 amino acids in length are preferred, with lengths of 15-30 amino acids particularly suited to some uses. Such peptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of peptides is commercially available from suppliers such as Perkin Elmer/Applied BioSystems Division (Foster City, Calif.), and may be operated according to the manufacturers instructions.

Peptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

In general, peptides (including fusion proteins) and polynucleotides as described herein are isolated. An "isolated" peptide or polynucleotide is one that is removed from its original environment. For example, a naturally occurring protein is isolated if it is separated from some or all of the coexisting materials in the natural system. Preferably, such peptides are at least about 90% pure, more preferably at least about 95% pure and most preferably at least about 99% pure. A polynucleotide is considered to be isolated if, for example, it is cloned into a vector that is not a part of the natural environment.

Antibodies

The term "antibody" is used in the broadest sense and specifically covers single anti-isoform monoclonal antibodies and anti-isoform antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

The invention provides antibodies that bind to isoforms. The most preferred antibodies will specifically bind to an isoform and will not bind (or will bind weakly) to non-isoform counterparts or non-cancerous specimens. Antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

Antibodies of the invention may be particularly useful in cancer diagnostic and prognostic assays, and imaging methodologies. Intracellularly expressed antibodies (e.g., single chain antibodies) may be therapeutically useful in treating cancers in which the expression of isoform is involved.

The invention also provides various immunological assays useful for the detection and quantification of isoforms. Such assays generally comprise one or more antibodies capable of recognizing and binding an isoform of the invention, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing isoforms are also provided by the invention, including but not limited to radioscintigraphic imaging methods using labeled antibodies. Such assays may be clinically useful in the detection, monitoring, and prognosis of isoform-expressing cancers.

Various methods for the preparation of antibodies are well known in the art. For example, antibodies may be prepared by immunizing a suitable mammalian host using an isoform or fragment thereof, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of isoforms may also be used, such as a GST-fusion protein. In another embodiment, an isoform may be synthesized and used as an immunogen.

The antibodies or fragments may also be produced, using current technology, by recombinant means. Regions that bind specifically to the desired regions of the isoform can also be produced in the context of chimeric or CDR grafted antibodies of multiple species origin. Humanized or human antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522 525; Riechmann et al., 1988, Nature 332: 323 327; Verhoeyen et al., 1988, Science 239: 1534 1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 18: 535 539).

Fully human monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45 64 (1993): Burton and Barbas, Human Antibodies from combinatorial libraries. Id., pp 65 82). Fully human monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607 614). This method avoids the in vitro manipulation required with phage display technology and efficiently produces high affinity authentic human antibodies.

Reactivity of antibodies with an isoform of the invention may be established by a number of well known means, including western blot, immunoprecipitation, ELISA, and FACS analyses using, as appropriate, isoforms, isoform-expressing cells or extracts thereof An antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the antibody can be selected in accordance with the intended use. Further, bi-specific antibodies specific for two or more isoform epitopes may be generated using methods generally known in the art. Homodimeric antibodies may also be generated by cross-linking techniques known in the art (e.g., Wolff et al., Cancer Res. 53: 2560 2565).

Polynucleotides of the Invention

The invention provides polynucleotides that encode one or more CSTC-targeting peptides, or an isoform of a component of a TCC, as described above. The encoding sequence for a particular isoform can be obtained from GenBank by searching the corresponding isoform name (see Table 1). Preferred polynucleotides comprise at least 15 consecutive nucleotides, preferably at least 30 consecutive nucleotides and more preferably 35 consecutive nucleotides, that encode a CSTC-targeting peptide or an isoform of a TCC, such as those listed in the Table below (see Example 1). Polynucleotides that are fully complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials. Portions of such CSTC-targeting polynucleotides can be useful as primers and probes for the amplification and detection of CSTC-targeting molecules.

Polynucleotides may comprise a native sequence (i.e., a sequence that encodes a CSTC-targeting peptide or isoform of a TCC as described above or a portion thereof) or may comprise a variant of such a sequence, or an aptamer. Polynucleotide variants contain one or more substitutions, additions, deletions and/or insertions such that activity (including specific binding) of the encoded peptide is not diminished, relative to a native peptide. Variants preferably exhibit at least about 60% identity, more preferably at least about 80% identity and most preferably at least about 90% identity to a polynucleotide sequence that encodes a native CSTC-targeting peptide or a portion thereof.

Two polynucleotide or peptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc. Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J, and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or peptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native protein (or a complementary sequence).

Suitable "moderately stringent conditions" include pre-washing in a solution of 5×SSC, 0.5% SDS. 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a peptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques such as hybridization, amplification and/or database sequence comparison).

Polynucleotides may be prepared using any of a variety of techniques known in the art, including, for example, oligonucleotide synthesis. Libraries can be screened with probes designed to identify the gene of interest or the peptide encoded by it. Screening the cDNA or other library with the selected probe may be conducted using standard procedures, such as those described in Sambrook et al., *Molecular Cloning: A Laboratory Manual* (New York: Cold Spring Harbor Laboratory Press. 1989).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a CSTC-targeting peptide, or portion thereof, provided that the DNA is incorporated into a vector with a suitable RNA polymerase promoter (such as T7 or SP6). Certain portions may be used to prepare an encoded peptide, as described herein. In addition, or alternatively, a portion may be administered to a patient such that the encoded peptide is generated in vivo (e.g., by transfecting antigen-presenting cells, such as dendritic cells, with a cDNA construct encoding a CSTC-targeting peptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine. Aptamers, oligonucleotides that recognize and bind to specific protein surfaces and therefore can interfere with the protein activity of co-regulator isoforms, are typically modified for therapeutic use. Where rapid clearance is desired, however, non-modified aptamers can be used in methods of the invention.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. Some embodiments of the peptides of the invention have been described herein with a cell penetrating peptide (CPP) incorporated into the peptide for facilitation of entry into a cell.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antisense and Inhibitory Nucleic Acid Molecules

The antisense molecules of the present invention comprise a sequence substantially complementary, or preferably fully complementary, to all or a fragment of a nucleic acid molecule that encodes a CSTC-targeting peptide and/or a cancer-specific isoform of a transcription modulator as described herein. Included are fragments of oligonucleotides within a coding sequence, and inhibitory nucleotides that inhibit the expression of CSTCs and/or cancer-specific isoforms of transcription modulators. Antisense oligonucleotides of DNA or RNA complementary to sequences at the boundary between introns and exons can be employed to prevent the maturation of newly-generated nuclear RNA transcripts of specific genes into mRNA for transcription. Antisense RNA, including siRNA, complementary to specific genes can hybridize with the mRNA for that gene and prevent its translation. The antisense molecule can be DNA, RNA, or a derivative or hybrid thereof, such as a chimeric gapmer. Examples of such derivative molecules include, but are not limited to, peptide nucleic acid (PNA) and phosphorothioate-based molecules such as deoxyribonucleic guanidine (DNG) or ribonucleic guanidine (RNG).

The antisense molecules of the invention are complementary to nucleic acid sequences that encode an isoform of the invention. The degree of homology necessary will depend on the particular polynucleotide of the invention. A homology of at least about 60% is sufficient for siRNAs, while larger antisense molecules and PCR primers require a homology of about 70% or greater.

Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

The design of siRNA molecules is known in the art and can be provided by vendors (e.g., Applied Biosystems/Ambion, Austin, Tex.). Beginning with the AUG start codon of the transcript, one can begin by scanning for AA dinucleotide sequences. Each AA and the 3' adjacent 19 nucleotides can be identified as potential siRNA target sites. This strategy for choosing siRNA target sites is based on the observation by Elbashir et al. (2001, EMBO J 20: 6877-6888) that siRNAs with 3' overhanging UU dinucleotides are the most effective. This is also compatible with using RNA pol III to transcribe hairpin siRNAs because RNA pol III terminates transcription at 4-6 nucleotide poly(T) tracts creating RNA molecules with a short poly(U) tail. In some embodiments, the selection of the siRNA target sequence is purely empirically determined, as long as the target sequence starts with GG and does not share significant sequence homology with other genes as analyzed by BLAST search. Alternatively, any accessible site in endogenous mRNA can be targeted for degradation by the synthetic oligodeoxyribonucleotide/RNase H method (Lee. N. S., et al. (2002) Nature Biotechnology 20: 500-505). Any accessible site identified in this fashion is then used as insert sequence in the U6 promoter-driven siRNA constructs. Typically, the siRNA expression cassette has a stem length of 19 nucleotides. siRNA stems ranging from 21 nucleotides-long to 25-29 nucleotides-long can also be useful in gene silencing.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule. Other modifications include the use of chimeric antisense compounds.

Chimeric antisense compounds of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures include, but are not limited to, U.S. Pat. Nos. 5,700,922 and 6,277,603.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compositions of the invention include oligonucleotides formed of homopyrimidines that can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99-125, 1990. Formation of the triple helix would interrupt the ability of the specific gene to undergo transcription by RNA polymerase. Triple helix formation using myc-specific oligonucleotides has been observed. See: Cooney, M, et al. Science 241:456-459.

Antisense sequences of DNA or RNA can be delivered to cells. Several chemical modifications have been developed to prolong the stability and improve the function of these molecules without interfering with their ability to recognize specific sequences. These include increasing their resistance to degradation by DNases, including phosphotriesters, methylphosphonates, phosphorothioates, alpha-anomers, increasing their affinity for binding partners by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Antisense compositions including oligonucleotides, derivatives and analogs thereof, conjugation protocols, and antisense strategies for inhibition of transcription and translation are generally described in: Antisense Research and Applications, Crooke, S. and B. Lebleu, eds. CRC Press, Inc. Boca Raton Fla. 1993; Nucleic Acids in Chemistry and Biology Blackburn, G, and M. J. Gait, eds. IRL Press at Oxford University Press, Inc. New York 1990: and Oligonucleotides and Analogues: A Practical Approach Eckstein, F. ed., IRL Press at Oxford University Press, Inc. New York 1991; which are each hereby incorporated herein by reference including all references cited therein which are hereby incorporated herein by reference.

Pharmaceutical Compositions

The invention provides CSTC-targeting peptides, cancer-specific isoforms of transcription modulators, polynucleotides, T cells and/or antigen presenting cells that are incorporated into pharmaceutical compositions. Pharmaceutical compositions comprise one or more such compounds and, optionally, a physiologically acceptable carrier. Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition can contain DNA encoding one or more of the peptides as described above, such that the peptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N. Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intradermal or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the delivered molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a peptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Cancers to be treated include, but are not limited to, melanoma, colorectal cancer, lung cancer (small and non-small cell carcinoma), hepatoma (primary liver cancer), pancreatic cancer, prostate cancer, brain tumors, including glioblastoma, astrocytoma and neuroblastoma, sarcomas, including chondrosarcoma, breast cancer, ovarian cancer, and teratocarcinoma.

Peptides or nucleic acid based drugs (e.g., antisense RNAs, siRNAs, mRNAs) can be delivered to cells via chemical means, biological means, carrier peptides, vectors, or physical delivery systems. Representative chemical means include, but are not limited to, specific chemical substances, including cationic polymers such as polyethylenimine (PEI) and cationic lipids. An example of a biological means of delivery is cell-penetrating peptides (CPPs). An exemplary carrier peptide is transportan. Vectors include plasmids and viruses, or cells. Representative physical delivery systems include, but are not limited to electrically-based systems and those using mechanical force, such as gene guns.

Isoforms of the invention can be targeted as members of protein complexes or as singular proteins by specific interaction with peptides recognizing only these isoforms. The activity of peptide in neutralizing the activity of the isoform can also be detected by using conventional proteomic methods (for example, immunoprecipitation, including chromatin immunoprecipitation (ChIP), reporter assays, immunodetection using specific antibodies) or by monitoring cellular activity.

Within certain embodiments, immunotherapy may be employed, such as active immunotherapy, in which treatment relies on the in vivo stimulation of the endogenous host immune system to react against tumors or infected cells with the administration of immune response-modifying agents (such as peptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a peptide provided herein. In a preferred embodiment, dendritic cells are modified in vitro to present the peptide, and these modified APCs are administered to the subject. T cell receptors and antibody receptors specific for the peptides recited herein may be cloned, expressed and transferred into other vectors or effector cells for adoptive immunotherapy. The peptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to alleviate, reduce, and cure or at least partially arrest symptoms and/or complications from the disease and/or to elicit an effective immune response to the specific antigens. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intraperitoneal, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart. In another embodiment, a dose is administered daily or once every 2 or 3 days over an extended period, such as weeks or months.

A suitable dose is an amount of a compound that, when administered as described above, is capable of promoting an anti-tumor response, and is at least 10-50% above the basal (i.e., untreated) level. Such response can be monitored, for example, by measuring reduction in tumor size or the level of anti-tumor antibodies in a patient or by vaccine-dependent generation of cytolytic effector cells capable of killing the patient's tumor cells in vitro. Such therapies should also be capable of causing a response that leads to an improved clinical outcome (e.g., more frequent remissions, complete or partial or longer disease-free survival) in patients as compared to untreated patients. In general, for pharmaceutical compositions and vaccines comprising one or more peptides, the amount of each peptide present in a dose ranges from about 100 µg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Diagnostic Methods

The invention provides a method for detecting cancer in a tissue comprising contacting the tissue with a molecule that recognizes and binds a CSTC or cancer-specific isoform of a transcription modulator (or TCC) described herein. The molecule can be, for example, a CSTC-targeting peptide, an antibody directed against a CSTC or cancer-specific isoform of a transcription modulator, or an oligonucleotide probe or antisense molecule directed against a cancer-specific molecule.

The tissue can be from a mammal, such as human, bovine, equine, canine, feline, porcine, and ovine tissue. The tissue is preferably a human. The tissue can comprise a tumor specimen, tissue specimen, body fluid specimen, including blood, ductal fluid, saliva, urine, cerebrospinal fluid, or other suitable specimen.

In one embodiment, the method comprises use of an ELISA type assay. In another embodiment, the method comprises use of quantitative PCR, or other assessment of the level of isoform present in the tissue. In some embodiments, the assay makes use of a histological specimen or culture preparation. Those skilled in the art will appreciate additional variations suitable for the method of detecting cancer in tissue through detection of a cancer-specific molecule in a specimen. Detection can be direct detection of the protein form of cancer-specific isoforms of co-regulators, or by detection of mRNA. For mRNA, typically RT-PCR based techniques are used, however, RNA can be detected also by northern blot analysis, RNase protection assay, dot blot, in situ hybridization, run-on-assays and the like. For protein-based assays, typically specific antibodies are used for immunocytochemical-histological analysis, immunoprecipitation analysis, ChiP analysis. Another option is to monitor protein activity, using cell-based assays. In one embodiment, the assay comprises determining the disappearance of the relevant protein function. For example, certain co-regulator isoforms act upon cancer cell survival. Blocking their activity would cause cancer cells stop to proliferating and induce programmed cell death.

This method can also be used to monitor levels of the cancer-specific molecule in tissue of a patient undergoing treatment for cancer. The suitability of a CSTC-targeted therapeutic regimen for initial or continued treatment can be determined by monitoring such levels using this method.

In some embodiments, the peptide and/or nucleic acid can be labeled, as desired for in vivo real-time imaging or other assays in which a detectable label facilitates identification of binding. Peptide or nucleic acids interfere with the synthesis or activity of co-regulator isoform and this can be monitored by conventional mRNA or protein identification techniques making use a detectable label unnecessary.

The invention additionally provides a method for identifying a molecule that inhibits proliferation of cancer cells. The method comprises contacting a candidate molecule with a CSTC and determining whether the candidate molecule disrupts the biological activity of the CSTC. Disruption of the biological activity of the CSTC is indicative of a molecule that inhibits proliferation of cancer cells. Representative molecules include proteins, peptides, aptamers and nucleotides.

Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be a polypeptide or polynucleotide specific for a cancer-specific molecule of the invention. The kit can also include containers containing nucleotide(s) for amplification of a target nucleic acid sequence and/or a container comprising a reporter-means, such as a biotin-binding protein, e.g., avidin or streptavidin, bound to a detectable label, e.g., an enzymatic, florescent, or radioisotope label. The kit can include all or part of an amino acid sequence of the sequences described herein, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

EXAMPLES

Example 1

Isolation and Sequencing of mRNAs Encoding for Isoforms of TCC Components

Identification of Isoforms of Transcriptional Co-Regulators in Melanoma Cells

RNA was isolated from human cancer cell lines and primary tumors using RNA isolation KIT (Qiagen). RT-PCR was used to identify isoforms of co-regulators.

First strand cDNAs were synthesized with reverse transcriptase (SuperscriptII, Life Technologies Inc.) using 5-10 µg of mRNA from different cell lines as a template. PCR reactions were performed in the volume of 25 µl containing one tenth of RT reaction as a template and GC-Rich PCR System or the Expand.™ Long Distance PCR System kit (Roche) according to manufacturers instructions. All amplified PCR products were sequenced and sequences analyzed to identify novel protein isoforms of components of TCCs.

TABLE 1

Protein sequences of identified isoforms of TCC components.

GTF: 51 isoforms
TAFs: 30 isoforms
SWI/SNF: 37 isoforms
MED: 80 isoforms
Co-activators/Co-repressors: 6 isoforms Full details of Table 1 are provided in a separate text document submitted herewith.

Example 2

Identification of Isoforms in Transcriptional Complexes: MudPIT Analysis

Nuclear extracts were prepared according to the method of Dignam et al. (1983) from parental HeLa cells and six HeLa cell lines stably expressing mammalian Mediator subunits human Nut2 (MED10) (Malik et al., 2000), mouse Med25 (MED9) (Tomomori-Sato et al., 2003), human Intersex (MED29) (Sato et al., 2003a), human LCMR1 (MED19) (Sato et al., 2003a), human AK007855 (MED28), or human CRSP70 (MED26), all with N-terminal FLAG epitope tags. Nuclear extracts were subjected to anti-FLAG agarose immunoaffinity chromatography performed essentially as described for purification of the TRAP/SMCC Mediator complex from FLAG-Nut2-expressing HeLa cells (Malik et al., 2000)

Phosphocellulose Chromatography

HeLa cell nuclear extracts (30 ml) were prepared according to the method of Dignam et al. (1983) and dialyzed against HEG buffer [20 mM HEPES-NaOH (pH 7.6), 0.1 mM EDTA, 1 mM DTT, and 10% (v/v) glycerol, 1 mM benzamidine, 0.25 mM PMSF, 2 g/ml aprotinin] to a conductivity equivalent to that of HEG containing 0.1 M KCl.

Following centrifugation for 30 min at 40,000 rpm in a Ti-45 rotor, the supernatant (130 mg of protein) was applied at two packed column volumes per hour to a phosphocellulose column (10 mg of protein per ml packed column bed volume) equilibrated in HEG containing 0.1 M KCl. The column was washed at the same flow rate with HEG containing 0.1 M KCl and eluted stepwise with HEG containing 0.3, 0.5, and 1.0 M KCl. One-fifth column volume fractions were collected. Protein eluted from the column with 0.5 M KCl and 1.0 M KCl was subjected to FLAG immunopurification as described above.

Identification of Mediator subunits and Mediator-associated proteins was accomplished using a modification of the MudPIT procedure described by Washburn et al. (2001). For each analysis, 60 µl aliquots of anti-FLAG agarose eluates were used.

Results

MudPIT analysis identified following isoforms of MED complex components from immunoprecipitated MED complexes:

MED1.3.

(SEQ ID NO: 4)
MKAQGETEESEKLSKMSSLLERLHAKFNQNRPWSETIKLVRQVMEKRVVM
SSGGHQHLVSCLETLQKALKVTSLPAMTDRLESIARQNGLGSHLSASGTE
CYITSDMFYVEVQLDPAGQLCDVKVAHHGENPVSCPELVQQLREKNFDEF

-continued
```
SKHLKGLVNLYNLPGDNKLKTKMYLALQSLEQDLSKMAIMYWKATNAGPL
DKILHGSVGYLTPRSGGHLMNLKYYVSPSDLLDDKTASPIILHENNVSRS
LGMNASVTIEGTSAVYKLPIAPLIMGSHPVDNKWTPSFSSITSANSVDLP
ACFFLKFPQPIPVSRAFVQKLQNCTGIPLFETQPTYAPLYELITQFELSK
DPDPIPLNHNMRFYAALPGQQHCYFLNKDAPLPDGRSLQGTLVSKITFQH
PGRVPLILNLIRHQVAYNTLIGSCVKRTILKEDSPGLLQFEVCPLSESRF
SVSFQHPVNDSLVCVVMDVQDSTHVSCKLYKGLSDALICTDDFIAKVVQR
CMSIPVTMRAIRRKAETIQADTPALSLIAETVEDMVKKNLPPASSPGERG
VYHWLESDPSSSHAATCLFDGRQHQEPPDAHEPS*
```

MED24.1.
(SEQ ID NO: 5)
```
MKVVNLKQAILQAWKERWSDYQWAINMKKFFPKGATWDILNLADALLEQA
MIGPSPNPILSYLKYAISSQMVSYSSVLTAISKFDDFSRDLCVQALLDIM
DMFCDRLSCHGKAEECIGLCRALLSALHWLLRCTAASAERLREGLEAGTP
AAGEKQLAMCLQRLEKTLSSTKNRALLHIAKLEEASLHTSQGLGQGGTRA
NQPTASWTAIEHSLLKLGEILANLSNPQLRSQAEQCGTLIRSIPTMLSVH
AEQMHKTGFPTVHAVILLEGTMNLTGETQSLVEQLTMVKRMQHIPTPLFV
LEIWKACFVGLIESPEGTEELKWTAFTFLKIPQVLVKLKKYSHGDKDFTE
DVNCAFEFLLKLTPLLDKADQRCNCDCTNFLLQECGKQGLLSEASVNNLM
AKRKADREHAPQQKSGENANIQPNIQLILRAEPTVTNILKTMDADHSKSP
EGLLGVLGHMLSGKSLDLLLAAAAATGKLKSFARKFINLNEFTTYGSEES
TKPASVRALLFDISFLMLCHVAQTYGSEVILSESRTGAEVPFFETWMQTC
MPEEGKILNPDHPCFRPDSTKVESLVALLNNSSEMKLVQMKWHEACLSIS
AAILEILNAWENGVLAFESIQKITDNIKGKVCSLAVCAVAWLVAHVRMLG
LDEREKSLQMIRQLAGPLFSENTLQFYNERVVIMNSILERMCADVLQQTA
TQIKFPSTGVDTMPYWNLLPPKRPIKEVLTDIFAKVLEKGWVDSRSIHIF
DTLLHMGGVYWFCNNLIKELLKETRKEHTLRAVELLYSIFCLDMQQVTLV
LLGHILPGLLTDSSKWHSLMDPPGTALAKLAVWCALSSYSSHKGQASTRQ
KKRHREDIEDYISLFPLDDVQPSKLMRLLSSNEDDANILSSPTDRSMSSS
LSASQLHTVNMRDPLNRVLANLFLLISSILGSRTAGPHTQFVQWFMEECV
DCLEQGGRGSVLQFMPFTTVSELVKVSAMSSPKVVLAITDLSLPLGRQVA
AKAIAAL
```

Example 3

Identification of Isoforms in Transcriptional Complexes: Biochemical Fractionation Materials and Methods
Preparation of Nuclear Extracts from Mammalian Cells
Collect cells from monolayer cultures.
1. Remove the culture medium from confluent monolayer cultures. Wash the cells by pipetting sufficient PBS to cover them, swirling gently, and pouring off the PBS. Scrape the cells into fresh PBS and pool in a graduated conical centrifuge tube.
2. Pellet the cells by centrifuging 10 min at 3000 rpm.
3. Decant the supernatants and discard. Using the graduations on the tube, measure the pcv.
4. Rapidly resuspend the cell pellets in a volume of hypotonic buffer □5 times the pcv.
Centrifuge the cells 5 min 3000 rpm and discard supernatant. Do this step quickly because proteins can leak out of the cell at this point and be discarded with the supernatant. This step removes salt from the PBS solution so that efficient swelling can occur in the next step; however, some swelling will occur during this step.
5. Resuspend the packed cells in hypotonic buffer to a final volume of 3 times the original pcv (step 3) and allow to swell on ice 10 min. For example, if an original pcv of 10 ml has swelled to 20 ml in step 4, only 10 ml of additional buffer is required at this step. The cells should swell at least 2-fold.
6. Transfer the cells to an Insulin syringe. Homogenize with ten up-and-down strokes. Perform the homogenization slowly, especially the down strokes.
7. Transfer cells to centrifuge tubes. Collect the nuclei by centrifuging 15 min at 4000 rpm (3300 g). Remove the supernatant and save for S-100 cytoplasmic extract preparation.

Extraction of Chromatin Complexes
8. Using the graduations on the tubes, measure the packed nuclear volume (pnv) from step 7. Resuspend the nuclei in a volume of low-salt buffer equal to 12 pnv. Resuspension of the nuclei with a small volume of low-salt buffer allows thorough rapid mixing of the nuclei during the addition of the high-salt buffer (step 9)
9. In a dropwise fashion, while stirring gently, add a volume of high-salt buffer equal to 12 the pnv (from step 8). The high-salt buffer must be added dropwise with frequent or continuous mixing. If it is added too quickly, local concentration of salt can become high and some nuclei will lyse. The final concentration of potassium chloride should be □300 mM.
10. Allow the nuclei to extract for 30 min with continuous gentle mixing. Mixing can be done using very gentle stirring on a magnetic stirrer or by tilting on a tiltboard.
11. Pellet the extracted nuclei by centrifuging 30 min at 14,500 rpm (25,000 g). Draw off the resulting supernatant. This is the nuclear extract.

Dialyze and Store the Extract
12. Place the nuclear extract in dialysis tubing. Dialyze against 50 vol of dialysis buffer until the extract reaches 100 mM KCl.
13. Remove the extract from the dialysis bag. Centrifuge the extract 20 min at 14.500 rpm. Discard the pellet. This will remove protein and nucleic acid that precipitates when the potassium chloride concentration is lowered during dialysis.
14. Determine the protein concentration of the supernatant. Aliquot into tubes if desired and rapidly freeze by submerging in liquid nitrogen. Store the extracts at ~80° C.

Dialysis Buffer
20 mM HEPES, pH 7.9 at 4° C.
20% glycerol
100 mM KCl
0.2 mM EDTA
0.2 mM PMSF*
0.5 mM DTT*

High-Salt Buffer
20 mM HEPES, pH 7.9 at 4° C.
25% glycerol
1.5 mM MgCl2
0.8, 1.0, 1.2, 1.4 or 1.6 M KCl
0.2 mM EDTA
0.2 mM PMSF*
0.5 mM DTT*
*Add ingredients immediately before use (see introductory note to reagents and solutions).

Hypotonic Buffer
10 mM HEPES, pH 7.9 at 4° C.
1.5 mM MgCl2
10 mM KCl
0.2 mM PMSF*
0.5 mM DTT*

Low-Salt Buffer
Prepare high-salt buffer, substituting 0.02 M KCl for 1.2 M KCl.
*Add ingredients immediately before use (see introductory note to reagents and solutions).

Fractionation of Chromatin Complexes
Pre-Cycling of P11 Resin
1. Stir resin into 25 volumes of 0.5 M NaOH for 5 minutes.
2. Wash with mQ until the filtrate pH is 11.0.
3. Stir resin into 25 volumes of 0.5 M HCl for 5 minutes.
4. Wash with mQ until the filtrate pH is above 3.0.

5. Transfer the pre-cycled PC immediately into 20 volumes of 5× concentrated buffer solution:
   100 mM Hepes pH 7.9
   20% v/v glycerol
   2.5 mM DTT
   1.0 mM EDTA
   0.5 M KCl
6. Titrate the slurry to the correct pH
7. Decant the supernatant.
8. Stir the PC into 20 volumes of the starting elution buffer
9. Leave for 3-4 minutes.
10. Repeat washing until pH is correct and storage at +4° C. for week.

Batch Purification of Transcription Complexes.

For 25 mg of protein it is necessary 1 ml bed volume of packed resin.

11. Add appropriate quality of pre-cycling resin to cell nuclear extract.
12. Rotate about 1 hour at +4° C.
13. Centrifuge 3 minutes at 2000 rpm at +4° C.
14. Supernatant—is flow through fraction, keep it at −80° C. until analysis.
15. Wash resin step by step increasing KCl concentration of elution buffer from 0.2 to 1.0 M, adding 2 volumes of buffer to 1 bed volume of PC. At every stage rotate resin for 30 minutes at +4° C. and pull down for 3 minutes at 2000 rpm. Collect fractions.

Elution Buffer:
20 mM Hepes pH 7.9
20% glycerol
0.2 mM EDTA
0.5 mM DTT
1×PIC
KCl 0.2 M-1.0 M Western Blot Analysis Western blot analysis was performed according to the protocol published in Ali Sadra, Tomas Cinek and John B. Imboden. "Multiple Probing of an Immunoblot Membrane Using a Non-Block Technique: Advantages in Speed and Sensitivity," *Analytical Biochemistry*, 278, 2000, p. 235-237 Briefly, 15 μg of protein samples were solubilized in SDS sample buffer and were subjected to 10% SDS-polyacrylamide gel electrophoresis. The proteins were then transferred onto PVDF membranes (Amersham) using Bio-Rad semi-dry blotter and standard Towbin buffer (10× concentrate (0.25 M Tris and 1.92 M Glycine in aqueous solution)). For further analysis the non-block technique was used, after the transfer of proteins onto the PVDF membrane, the membrane was air-dried for 15 min and went through three cycles of 50% methanol-water hydration. The blotted membrane was then left in 100% methanol for 2 min and allowed to dry completely in an incubator for 10 min at 37° C. After the membrane was dry, it was incubated with the primary antibody solution (made in 3% nonfat milk-TBS-T) overnight at +4° C. The membrane was then washed 3 times with TBS-T for 10 min per each wash, followed by incubation with the secondary antibody solution (made in 3% nonfat milk-TBS-T) for 30 min at room temperature and with gentle shaking. Following three washes of 20 min each with TBS-T, the ECL detection (Amersham) of the signals of the target proteins was performed.

Antibodies:
Primary Antibodies:
Baf57 (C-20) against an epitope within the internal region of human Baf57, (Santa Cruz), dilution 1:500;
P62/THIIH1 (mouse monoclonal, MAb 3C9, kind gift of J. M. Egly), dilution 1:10 000;
Med-16/TRAP 95 (C-19) against an epitope within the C-terminus of human TRAP 95, dilution 1:500.

Secondary antibodies (anti-goat for Baf57 and Med-16/TRAP 95, anti anti-mouse for p62/THIIH1), dilution 1:100 000.

Results

Fractionation of nuclear extracts following Western blotting to detect isoforms of TCCs dearly showed that isoforms are present in transcription complexes and can be fractionated similar to wild type isoforms.

BAF Complexes

Fractionation of BAF complexes was analyzed using P11 phosphocellulose. Western blot analysis of BAF fractions identified isoforms and wild type BAF57 in the same fractions that is an indication that BAF57 isoforms are present in the active BAF57 complex.

Figure 1:
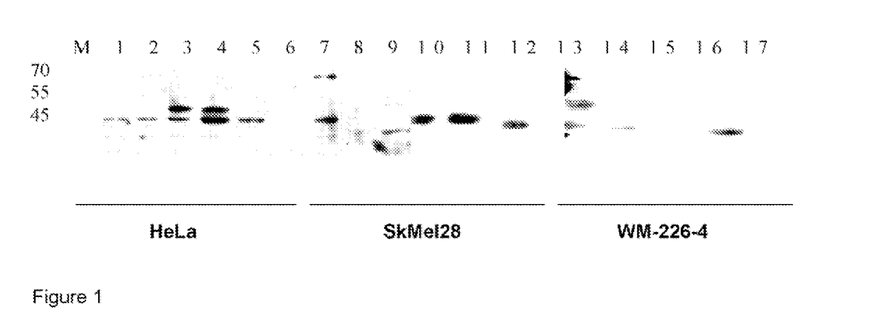

FIG. 1 shows the results of analysis of BAF complexes from HeLa and human melanoma SK-Mel 28 and WM266-4 cells. Aliquots of HeLa, SKMel28 and WM 266-4 cell nuclear extracts were chromatographed on ion-exchange PE11 column containing. After washing the column extensively with buffer containing 0.1M KCl, bound proteins were eluted with buffer containing 0.2 (lanes 2, 8 and 14), 0.3M KCl (lanes 3, 9 and 15), 0.5M KCl (lanes 4, 10 and 16), 0.75MKCl (lanes 5, and 11) and 1.0M KCl (lanes 6, and 12). Initial "flow through" is depicted on lanes 1, 7 and 13.

GTF Complex

Fractionation of GTF complexes was analyzed using P11 phosphocellulose. Western blot analysis of TFIIH subunit p62 identified isoforms and wild type p62 in the same fractions that is an indication that TFIIH subunit isoforms are present in the active complex.

Figure 2:
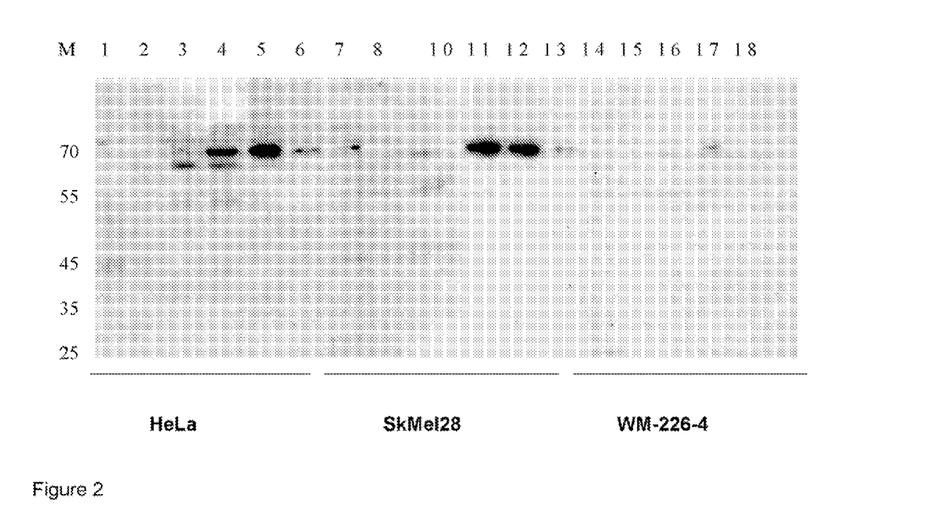
FIG. 2. Analysis of fractionation of GTF complex by detecting p62 (TFIIH subunit) using Western blot detection from HeLa cells and human melanoma SK-Mel 28 and WM266-4 cells. Aliquots of HeLa, SKMel28 and WM 266-4 cell nuclear extracts were chromatographed on ion-exchange PE11 column. After washing the column extensively with buffer containing 0.1M KCl, bound proteins were eluted with buffer containing 0.2 (lanes 2, 8 and 14), 0.3M KCl (lanes 3, 9 and 15), 0.5M KCl (lanes 4, 10 and 16), 0.75MKCl (lanes 5, 11 and 17) and 1.0M KCl (lanes 6, 12 and 18) initial "flow through" is depicted on lanes 1, 7 and 13.

FIG. 2 shows the results of analysis of fractionation of GTF complex by detecting p62 (TFIIH subunit) using Western blot detection from HeLa cells and human melanoma SK-Mel 28 and WM266-4 cells. Aliquots of HeLa, SKMel28 and WM 266-4 cell nuclear extracts were chromatographed on ion-exchange PE11 column. After washing the column extensively with buffer containing 0.1M KCl, bound proteins were eluted with buffer containing 0.2 (lanes 2, 8 and 14), 0.3M KCl (lanes 3, 9 and 15), 0.5M KCl (lanes 4, 10 and 16), 0.75MKCl (lanes 5, 11 and 17) and 1.0M KCl (lanes 6, 12 and 18). Initial "flow through" is depicted on lanes 1, 7 and 13.

MED Complex

Fractionation of MED complex was analyzed using P11 phosphocellulose. Western blot analysis of MED subunit MED16 identified isoforms and wild type MED16 in the same fractions that is an indication that MED subunit isoforms are present in the active complex.

Figure 3:
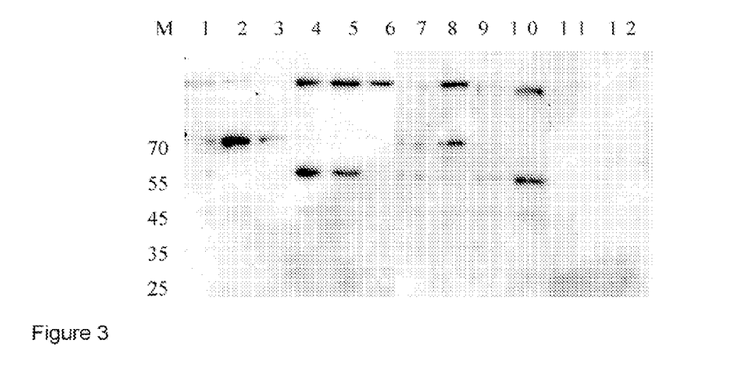
FIG. 3. Mediator complex purification conditions were assessed by detecting MED-16 in NER fractions from HeLa cells as compared to melanoma SK-Mel 28 cells. Aliquots of HeLa and SKMel28 cell nuclear extracts were chromatographed on ion-exchange PE11 column. After washing the column extensively with buffer containing 0.1M KCl, bound proteins were eluted with buffer containing 0.2 (lanes 2 and 8), 0.3M KCl (lanes 3 and 9). 0.5M KCl (lanes 4 and 10), 0.75MKCl (lanes 5 and 11) and 1.0M KCl (lanes 6 and 12). Initial "flow through" is depicted on lanes 1 and 7.

FIG. 3 shows results of assessment of mediator complex purification conditions by detecting MED-16 in NER fractions from HeLa cells as compared to melanoma SK-Mel 28 cells. Aliquots of HeLa and SKMel28 cell nuclear extracts were chromatographed on ion-exchange PE11 column. After washing the column extensively with buffer containing 0.1M KCl, bound proteins were eluted with buffer containing 0.2 (lanes 2 and 8), 0.3M KCl (lanes 3 and 9), 0.5M KCl (lanes 4 and 10), 0.75MKCl (lanes 5 and 11) and 1.0M KCl (lanes 6 and 12). Initial "flow through" is depicted on lanes 1 and 7.

Example 4

Binding of Peptide BAF57p12 to Isoform of BAF57iso

Materials and Methods

Protein purification. We have cloned and expressed BAF57, BAF57 iso, into pGEX-4T-1 (N-terminal GST) expression vector and expressed both wild type and isoform of BAF57

Expression of proteins was induced 8 hours at 300 C with 1 mM IPTG. Following induction cells were pelleted and washed in native extraction buffer.

10 mM Na2HPO4, 1.8 mM KH2PO4 (pH7.3)
140 mM NaCl
2.7 mM KCl
1% Triton X100
Protease inhibitor cocktail (Roch Diagnostics, complete, cat #11 836 145 001)

GST-Baf57 and GST-BAF57iso protein purification: Cells were lysed using sonication: 3×15 sec on ice, letting lysate to cool between sonications.

Lysate was centrifuged 10 min at 11 000×g to remove insoluble material. Supernatant was transferred to new tube.

100 µl of a 50% slurry of Glutathione Sepharose 48 (GE Healthcare) was added to each lysate supernatant and mixed gently for 5 min at RT.

500 µl of 1× extraction buffer without Triton X100 was added, vortexed briefly and centrifuged for 1 min to sediment the sepharose beads.

Supernatants were discarded and washing was repeated 2 times for a total of 3 washes.

The fusion protein was eluted by the addition of 30 µl of glutathione elution buffer (10 mM reduced glutathione, 50 mM Tris-HCl, pH 8.0) and incubated for 5 min RT Solutions were centrifuged for 5 min max rpm and supernatant transferred to fresh tubes.

Purity proteins was analyzed using SDS PAGE and Western blot using antibodies against BAF57 that recognize both wild type and isoform of BAF57.

Binding studies. We used GST-BAF57 and GST-BAF57iso proteins extracted and purified using native conditions to conduct binding studies.

Figure 4:
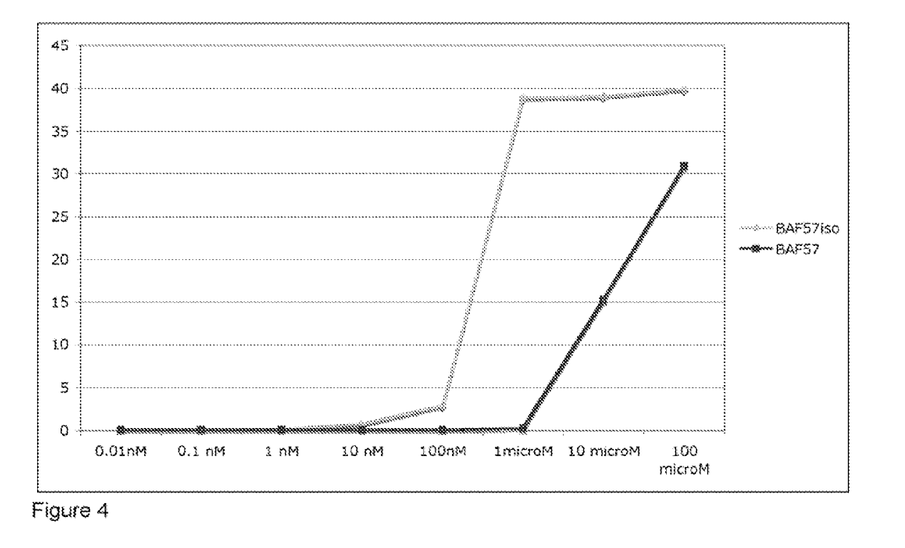
FIG. 4. Binding of peptide BAF57p12 to GST-BAF57 and GST-BAF57iso purified proteins in solution. Binding is represented as fluorescence intensity of released peptide in arbitrary units.

Initially fluorescein labeled peptide BAF57p12 was used to analyze its binding to GST-BAF57 and GST-BAF57iso bound to glutathione sepharose or in solution following binding to glutathione sepharose. Both protocols gave us similar results, peptide BAF57p12 binds to BAF57iso with high affinity but it also binds to BAF57, however the affinity is lower (FIG. 4). These experiments were done using peptides that were synthesized 1.5 years previously.

Binding of peptide to matrix bound proteins. Matrix bound proteins (10 µg/50 µl) were incubated with different concentrations of labeled peptides (0.01 nM-10 µM) in binding buffer (10 mM phosphate, 50 mM NaCl, 5 mM MgCl2, 2 mM spermidine, 0.3 mM DDT, pH 7.9) for 15 min at room temperature. Following incubation, matrix was washed with an incubation buffer 3 times of 10 volumes. Bound fluorescence was detected following release of protein from the matrix using 10 mM reduced glutathione, 50 mM Tris-HCl, pH 8.0.

Binding of peptides to proteins in solution. Purified proteins at concentration 10 µg/100 µl were mixed with labeled peptides (0.01 nM-10 µM) in binding buffer (10 mM phosphate, 50 mM NaCl, 5 mM MgCl2, 2 mM spermidine, 0.3 mM DDT, pH 7.9) for 15 min at room temperature. Following incubation a capture reagent (50 µl, Glutathione Sepharose 4B (GE Healthcare) was added and incubate for 20 min at room temperature. Following washing (5 times) with binding buffer bound proteins was released using 10 mM reduced glutathione, 50 mM Tris-HCl, pH 8.0.

Surface Plasmon Resonance analysis. To analyze binding of BAF57p12 to GST-BAF57 and GST-BAF57iso purified proteins we also used Surface Plasmon Resonance analysis using Biacore 3000 system at University of Helsinki (Finland). With this system, molecules of interest (ligands—proteins GST-BAF57 and GST-BAF57iso) were immobilized on a sensor surface, and binding partners (analytes—peptide BAF57p12) were then passed over it in a mobile aqueous phase. Their interaction on the sensor surface can subsequently be monitored in real time without the use of labels. Proteins GST-BAF57 and GST-BAF57iso were immobilized by amine coupling methods, according to the instruction manual for the Biacore 3000 CM5 sensor chip, which utilizes a primary amino group of proteins for covalent attachment to the matrix. To estimate protein-peptide interactions, the affinity of the interaction (the equilibrium dissociation constant (KD), was determined from the level of binding at equilibrium as a function of the sample concentrations by BIAevaluation version 4.1 software (Biacore, Inc.). Peptide BAF57p12 was dissolved in running (binding buffer) buffer, and binding experiments were performed at 25° C. in running buffer with a flow rate of 20 µl/min. Our preliminary analysis results show that BAF57p12 binding to GST-BAFiso has a Kd value of $5.5 \times 10^{-7}$ M and BAF57p12 binding to GST-BAF has a Kd value of $3 \times 10^{-4}$ M, These results confirm our data obtained by using fluorescein labeled peptides.

Example 5

Expression of Isoforms in Various Cancers

This example demonstrates the expression of isoforms of transcription factor complex (TCC) components in various types of cancer. Expression was determined by RT-PCR analysis of clinical cancer samples as well as numerous cell lines. Semiquantitative RT-PCR analysis was followed by DNA sequence analysis of PCR fragments. Analysis of normal tissues and non-cancerous cell lines revealed no expression of these isoforms, indicating that their expression is cancer-specific Table 2 below lists the types of cancers shown to express various isoform genes.

TABLE 2

| Expression of isoforms of TCC components in different cancer types | |
|---|---|
| Gene | Expression of isoforms in cancers |
| MED24 | melanoma, colorectal cancer, glioblastoma |
| MED1 | melanoma, colorectal, glioma, lung |
| MED4 | melanoma, colorectal, lung, glioma |
| MED12 | melanoma, colorectal, breast, glioma |
| MED13 | lung, breast |
| MED14 | ovarian, breast, liver |
| MED15 | chondrosarcoma, prostate, |
| MED28 | colorectal, breast |
| MED30 | colorectal, breast, neuroblastoma, glioma |
| BAF57 | melanoma, colorectal cancer, glioblastoma |
| BAF250 | colorectal, breast, neuroblastoma, glioma |
| BAF155 | lung, breast, prostate |
| BAF170 | lung, breast, prostate |
| BAF60 | lung, teratocarcinoma |
| BAF53 | colorectal, breast |
| BAF47 | glioma, neuroblastoma, prostate |
| TAF1 | lung, hepatoma |
| TAF4 | neuroblastoma, glioma, pancreatic |
| TAF7L | breast, prostate |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08664359B2). An electronic copy of the "Sequence Listing" will also be available from the USPTO upon request and payment of the fee set forth in 37 CFR 1.19(b)(3).

What is claimed is:

1. An isolated or recombinant cancer-specific polypeptide comprising a polypetide selected from the group of polypeptides consisting of SEQ ID NO: 100-107 and SEQ ID NO: 110.

2. The cancer-specific polypeptide of claim 1, which is a fusion protein comprising the cancer-specific polypeptide fused with a heterologous peptide.

3. The fusion protein of claim 2, wherein the heterologous peptide is selected from the group consisting of SEQ ID NO: 1-3.

4. The polypeptide of claim 1, and a pharmaceutically acceptable carrier.

5. A method for detecting cancer in a tissue specimen comprising:
    (a) contacting the specimen with an antibody that specifically binds a polypeptide of claim 1;
    (b) assaying for binding of the antibody to the polypeptide of claim 1, wherein binding of the antibody is indicative of cancer, and wherein the cancer is melanoma, colorectal cancer, lung cancer, hepatoma, prostate cancer, gliomas, glioblastoma, breast cancer, or ovarian cancer.

6. A method for monitoring cancer in a subject, the method comprising:
    (a) contacting a tissue specimen obtained from the subject with an antibody that specifically binds a polypeptide of claim 1;
    (b) measuring the amount of the polypeptide of claim 1 present in the specimen; and
    (c) comparing the amount of the polypeptide of claim 1 present in the specimen to the amount of said polypeptide determined under a previous condition, wherein a change in the amount of the polypeptide is indicative of a change in the progression of the cancer, and wherein the cancer is melanoma, colorectal cancer, lung cancer, hepatoma, prostate cancer, gliomas, glioblastoma, breast cancer, or ovarian cancer.

7. The method of claim 6, wherein the measuring of step (b) comprises determining the percentage of cancer cells in the tissue specimen to which the antibody binds and/or determining the quantity of binding of the antibody in the tissue specimen.

8. The method of claim 5, wherein the antibody is labeled with a detectable marker.

9. The method of claim 6, wherein the antibody is labeled with a detectable marker.

10. An isolated or recombinant polypeptide comprising a polypeptide selected from the group consisting of SEQ ID NO: 100-104.

11. The polypeptide of claim 10, which is a fusion protein comprising the polypeptide fused with a heterologous peptide.

12. The polypeptide of claim 1, having the amino acid sequence shown in SEQ ID NO: 100.

13. The polypeptide of claim 1, which is a recombinant polypeptide.

14. The polypeptide of claim 10, which is a recombinant polypeptide.

15. The method of claim 5, wherein the assaying comprises radioimmunoassay, enzyme-linked immunosorbent assay or enzyme-linked immunofluorescent assay.

16. The method of claim 6, wherein the measuring comprises radioimmunoassay, enzyme-linked immunosorbent assay or enzyme-linked immunofluorescent assay.

\* \* \* \* \*